(12) United States Patent
Whittall et al.

(10) Patent No.: US 12,263,258 B2
(45) Date of Patent: Apr. 1, 2025

(54) SANITISER

(71) Applicant: AIRDRI LIMITED, Oxford (GB)

(72) Inventors: Steve Whittall, Oxford (GB); Raj Gollatotla, Oxford (GB); Francesco Anastasi, Oxford (GB); Berran Hooper, Oxford (GB)

(73) Assignee: AIRDRI LIMITED, Oxford (GB)

( * ) Notice: Subject to any disclaimer, the term of this patent is extended or adjusted under 35 U.S.C. 154(b) by 0 days.

(21) Appl. No.: 18/026,284

(22) PCT Filed: Sep. 15, 2021

(86) PCT No.: PCT/GB2021/052395
§ 371 (c)(1),
(2) Date: Mar. 14, 2023

(87) PCT Pub. No.: WO2022/058729
PCT Pub. Date: Mar. 24, 2022

(65) Prior Publication Data
US 2023/0355816 A1 Nov. 9, 2023

Related U.S. Application Data

(63) Continuation of application No. 17/337,948, filed on Jun. 3, 2021.

(30) Foreign Application Priority Data

Sep. 15, 2020 (GB) .................................... 2014526

(51) Int. Cl.
*A61L 2/14* (2006.01)
*A47K 10/48* (2006.01)
*A61L 2/00* (2006.01)

(52) U.S. Cl.
CPC ............. *A61L 2/0082* (2013.01); *A47K 10/48* (2013.01); *A61L 2/14* (2013.01); *A61L 2202/11* (2013.01); *A61L 2202/15* (2013.01)

(58) Field of Classification Search
CPC ............. A61L 2/14; A61L 2/0082; A61L 9/22
See application file for complete search history.

(56) References Cited

U.S. PATENT DOCUMENTS

2007/0207054 A1\* 9/2007 Langford ................ A61L 2/206
422/26
2011/0277342 A1\* 11/2011 Ishii ....................... A47K 10/48
34/526

(Continued)

FOREIGN PATENT DOCUMENTS

CN 208355805 U 1/2019
KR 20100058088 A 6/2010

OTHER PUBLICATIONS

International Search Report and Written Opinion received in PCT/GB2021/052395 mailed Dec. 8, 2021, 10 pages.

(Continued)

*Primary Examiner* — Donald R Spamer
(74) *Attorney, Agent, or Firm* — Meunier Carlin & Curfman LLC

(57) ABSTRACT

The present invention provides a sanitiser (10) for sanitising a user, having a plasma generator (20), for generating a plasma (22), a reservoir (30), for storing plasma (22) generated by the plasma generator 20 and having one or more inlets (32) connected to the plasma generator (20) and a first and second outlet (34), (36). One or more fluid movers (40), (42) cause movement of the plasma (2) from the first and second outlets under the control of a controller (50) such as to cause the flow of plasma (22) out of one or other or both of said outlets (34), (36).

27 Claims, 6 Drawing Sheets

(56) References Cited

U.S. PATENT DOCUMENTS

| | | | | |
|---|---|---|---|---|
| 2012/0261590 A1* | 10/2012 | Boyle | ...................... | A61L 2/08 |
| | | | | 250/453.11 |
| 2013/0226073 A1* | 8/2013 | Kummerfeld | ............. | A61L 2/14 |
| | | | | 604/23 |
| 2013/0232807 A1* | 9/2013 | Robert | ...................... | B03C 3/70 |
| | | | | 422/186.04 |
| 2013/0272929 A1 | 10/2013 | Pelfrey et al. | | |
| 2017/0021043 A1* | 1/2017 | Baek | ........................ | A61L 2/14 |

OTHER PUBLICATIONS

Combined Search and Examination Report received in United Kingdom Application No. GB2014526.4 dated Mar. 16, 2021, 6 pages.

Office Action issued for U.S. Appl. No. 17/337,948, dated Mar. 28, 2024.

* cited by examiner

SANITISER

CROSS-REFERENCE TO RELATED APPLICATIONS

The present disclosure is the national phase under 35 U.S.C § 371 of PCT/GB2021/052395 filed on Sep. 15, 2021, which claims priority to U.S. patent application Ser. No. 17/337,948 filed Jun. 3, 2021 and United Kingdom Patent Application No. 2014526.4 filed Sep. 15, 2020, each of which is incorporated herein by reference in their entireties.

FIELD

The present invention relates to a sanitising apparatus. More particularly to a sanitizing apparatus for sanitizing all or part of a user using plasma created by ultraviolet light. Aspects of the invention may be combined with a dryer system to create a combined drier/sanitiser.

BACKGROUND

Sanitising after touching potentially contaminated surfaces concerns many people. Current government advice is to wash hands and contact surfaces frequently using soap or use greater than 70% alcohol sanitizing products to reduce transmission of bacterial and viral pathogens. To be effective when washing with soap and water government advice recommends a minimum of 20 seconds is spent washing hands and that up to a 10-step process is used to ensure that all surfaces of the hands are sanitised.

After washing a user needs to dry themselves. Conventional cotton towelling is not sterile after the first use, disposable paper towels are expensive, non-recyclable and require constant attention to ensure stocks are maintained and used towels are disposed of. Similarly, alcohol sanitizer is both expensive and requires monitoring to ensure stocks are maintained. Standard air driers are available as a non-contact solution; however, they provide no further sanitizing action.

Conventional air sanitizing units employ filters and ultraviolet light and ultraviolet photocatalytic oxidation (PCO) to sanitise air that is circulated. Short wavelength ultraviolet light (UV-C) penetrates micro-organisms such as virus and bacteria to kill or deactivate them through disrupting their nuclear material leaving them unable to perform their intended function. Ultraviolet photocatalytic oxidation creates hydroxyl radicals that can be circulated in the ambient air that also act to sanitise and super oxide ions that cause small particles to clump into clusters and remove them from the air.

The Radic8 Viruskiller air purifier and the Sterillo™ Hand Dryer use UV-C and PCO to sterilise ambient air and surrounding surfaces however neither are capable of sanitising a user in a convenient time period. American Dryer's ExtremeAir™ CPC utilises as cold plasma generator claimed to produce hydroxyl ions that are expelled in the direction of a user at a claimed 221 mph, therefore it is questionable how effective ions at such a low concentration and high velocity are at sanitizing a user's hands.

In addition to the above, it is known to provide hand driers with a sanitising arrangement, but such tend not to provide an effective low maintenance sanitiser capable of sanitising a user or for both a user and the ambient surroundings.

SUMMARY OF INVENTION

Therefore, aspects and/or embodiments seek to provide sanitised and sanitising air and plasma for sanitizing a user and the ambient surroundings of the sanitiser. Further embodiments may also provide air for drying the user's hands.

According to a first aspect, there is provided a sanitiser that may have an external casing and a first portion and a second portion. A plasma generator, for generating a plasma may be included. The plasma generator may be connected to a reservoir, for storing plasma generated by the plasma generator. The sanitiser may have one or more inlets connected to the plasma generator and a first and a second outlet. The sanitiser may have one or more fluid movers, for causing movement of the plasma. A controller may control the one or more fluid movers such as to cause the flow of plasma out of one or other or both of said outlets.

In an embodiment, the reservoir can provide storage in which plasma can be accumulated to allow sufficient plasma to be directed to the user to effectively sanitise the user in an acceptable amount of time to the user.

Optionally, the plasma generator is contained within the reservoir to directly fill the reservoir with plasma when required. There may be a first outlet towards an upper portion of the sanitiser. The outlet positioned for directing plasma generally outwardly and downwardly from the sanitiser.

In some embodiments, the first outlet towards the upper portion configured to direct plasma outwardly and downwardly can provide the advantage of the plasma being distributed around the environment in which the sanitiser is located. Thereby providing a sanitising effect on the air and surfaces in said environment. In an alternative embodiment the sanitiser may include a drier. This provides the dual benefit of drying a user after washing and consuming the time required to build up sufficient plasma in the reservoir to sanitise the user. The drier may be a jet drier for creating a jet of air and may further include an outlet for directing said air towards a user. The second outlet of the reservoir may be positioned proximal to the drier outlet for directing plasma towards the user.

In an alternative embodiment the drier may include a heater for heating air and an outlet for directing said heated air to towards a user. Wherein, the second outlet of the reservoir may be positioned proximal to the drier outlet for directing plasma towards the user.

In a further embodiment the second outlet from the reservoir may surround the drier outlet. Thereby providing no perceptible shift in the supply direction of the fluid provided to the user.

In an alternative embodiment the second outlet may include an outlet plenum comprising a plenum inlet and a plenum outlet. The plenum outlet may be offset from the inlet to slow the velocity and control the direction of plasma directed to the user. Thereby, providing increased contact between the user and the plasma provided by the machine and enhancing the sanitising effect.

In a preferred embodiment the controller may be operable in a first mode to cause the operation of the one or more fluid movers such as to cause the flow of plasma out of the first outlet alone. Therefore, advantageously sanitising the ambient surroundings of the sanitiser.

In a further embodiment the controller may be operable in a second mode to prevent operation of the one or more fluid movers such as to store plasma in said reservoir. Allowing a high quantity of dense plasma to be generated by the plasma generator to accumulate in the reservoir in preparation for sanitising a user in the manner described in the third or fourth modes below.

In a further embodiment the controller may be operable in a third mode to cause the operation of the one or more fluid movers such as to cause the flow of plasma out of the second outlet alone.

In a further embodiment the controller may be operable in a fourth mode to cause the operation of the one or more fluid movers such as to cause the flow of plasma out of both the first and second outlets simultaneously.

In an embodiment the controller may be operably connected to the presence sensor and to the one or more fluid movers for ceasing the operation thereof and, thereby, preventing flow of plasma from said reservoir for a period of time upon the detection of a user. Therefore, allowing a contact free operation by the user and reducing the chance of transmission of pathogens by touch.

In an alternative embodiment the controller may be operably connected to the hand drier for detecting the operation thereof. The controller may be operably connected to the presence sensor and to the one or more fluid movers for allowing the flow of plasma from said reservoir out of said second outlet and towards the user upon cessation of the flow of air from the hand drier.

In a further embodiment the controller may be operable upon receipt of a signal from the presence sensor to operate the one or more fluid movers to cause plasma to be directed out of said first outlet when no user is detected.

In an alternative embodiment the controller may be operable upon receipt of a signal from the presence sensor to operate the one or more fluid movers to cause plasma to be directed out of said first outlet when a user is detected.

In a further embodiment the one or more air movers may comprise one or more fans. A first fan of said one or more fans may be at the first outlet to the reservoir. A second fan of said one or more fans may be at the second of said outlets to the reservoir. Alternatively, the one or more fluid movers from the reservoir may comprise a single bi-directional fan.

In a further embodiment said one or more inlets to the reservoir may comprise one or other of the first and second outlets. Therefore, requiring fewer components and a simpler fluid flow through the sanitiser.

In an alternative embodiment the sanitiser may further include a timer that may be connected to the controller for causing the operation of the one or more fluid movers after the cessation of flow from the hand drier.

In a further embodiment the sanitiser may include a display for informing the user when the sanitising process is complete. The display may include a plurality of LEDs for indicating the time remaining until the sanitising process is complete. It is important that the full reservoir of plasma is directed at the user for the maximum sanitising effect. The display will clearly indicate to the user the relative time remaining until sanitising is complete to ensure the user remains for the full process.

In a further embodiment the sanitiser may include a gas sensor for detecting the concentration of a particular gas. The controller may be operably connected to the gas sensor. The controller may include a comparator for comparing a gas concentration threshold for the particular gas with the concentration of the particular gas detected by the gas sensor. The controller may be operable to activate or deactivate the plasma generator when the concentration of the particular gas is at or passes the gas concentration threshold. The controller may be operable to deactivate the plasma generator if the concentration of the particular gas is at or above the gas concentration threshold. The particular gas may be ozone.

The gas sensor allows the dryer to respond to the changing concentration of gasses in the air. In particular it is advantageous to control the concentration of ozone that can result from the super oxide ions created by the plasma generator.

In an embodiment the sanitiser may be for sanitising the hands of a user.

In an embodiment the drier may be a hand drier for drying the hands of a user.

BRIEF DESCRIPTION OF DRAWINGS

Aspects of the present invention will now be described, by way of example only and with reference to the accompanying drawings having like-reference numerals, in which.

SPECIFIC DESCRIPTION

Figure 1:
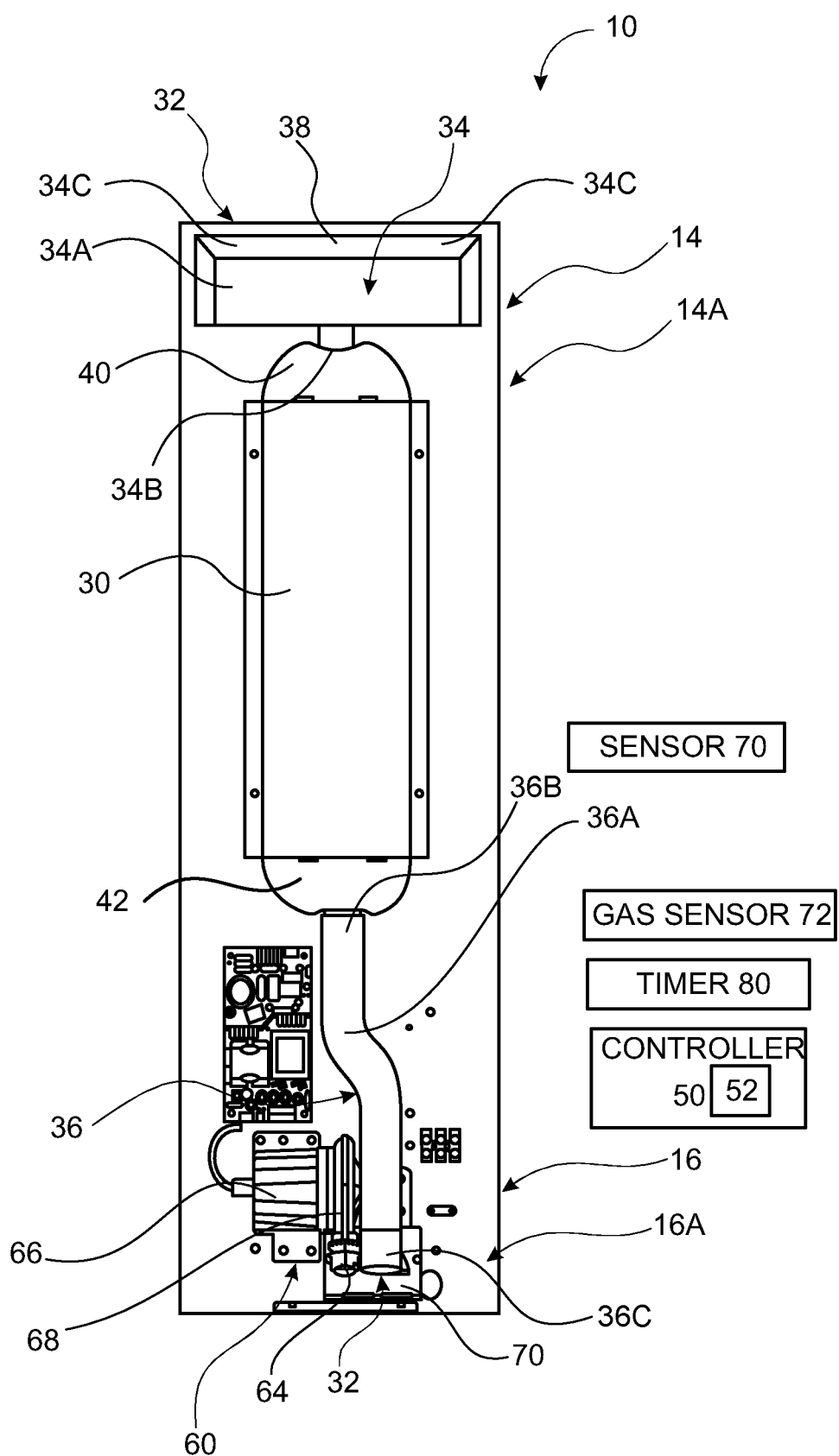
FIG. 1 shows the steriliser including a high-speed jet drier with the external casing removed.

Referring to FIG. 1, a first embodiment will now be described. From FIG. 1 it can be appreciated that the sanitiser 10 may include a reservoir 30, connected to a plasma generator 20 (not shown in FIG. 1) for generating plasma 22. One or more inlets 32 (not shown in FIG. 1) may be connected to the plasma generator 22. The reservoir 30 may have a first outlet 34 that may include a first duct 34A and a second outlet 36 that may include a second duct 36A, all are preferably fluidly connected to one or more inlets 32 for providing a passage for fluid from the one or more inlets 32 to outlets 34,36. The outlet 34 has a first end 34B connected to the reservoir 30 and a second end 34C open to the environment surrounding or outside the sanitiser 10. The two ends 34B, 34C may be connected by the duct 34A. The outlet 36 has a first end 36B connected to the reservoir 30 and a second end 36C open to the air surrounding or outside the sanitiser 10. The two ends 36B, 36C may be connected by the duct 36A.

The reservoir 30 maybe sealed apart from the one or more inlets 32 and outlets 34,36 for collecting and storing plasma 22 generated by the plasma generator 20. In a preferred arrangement the plasma 22 generated by the plasma generator 20 is in the form of a gaseous plasma 22. The fluid entering the one or more inlets 32 is air that is provided to the plasma generator 20 from which the plasma generator 20 generates plasma 22. For the purposes of this document plasma 22 is the fluid provided to and supplied by the outlets 34, 36 that may include a mixture of plasma 20 generated by the plasma generator 20 and air.

The first outlet 34 of the reservoir 30 may further include a divergent outlet 38 for providing plasma 22 from the reservoir 30 to the external casing 12 and the ambient surroundings for sanitising the external casing 12, the air and ambient surroundings. The ambient surroundings may be the area local to the sanitiser 10 or the room in which the sanitiser 10 is located including the air and surfaces in the area. The second outlet 36 of the reservoir 30 may include the duct 36A connecting the first end 36B and the second end 36C for providing and directing plasma to a user to sanitise the user.

The first outlet 34 may be situated in a first portion 14 of the sanitiser 10 and the second outlet 36 may be situated in a second portion of the sanitiser 10. In FIG. 1 it can be seen that the first outlet 34 may include a divergent outlet 38 that may be located towards the upper portion 14A of the sanitiser 10. In a preferred arrangement the divergent outlet 38 directs plasma 22 outwardly and downwardly for sanitising the external casing and/or surroundings. It will be appreciated that whilst in FIG. 1 the divergent outlet 38 of the first outlet 34 is paced towards the upper portion 14A of the sanitiser 10 the divergent outlet 38 can be placed at a lower portion 16B of the sanitiser or another point suitable for providing plasma 22 to the ambient surroundings. Similarly, the second outlet 36 is situated in the second portion 16 of the sanitiser 10. Whist in FIG. 1 the outlet 36 is in the lower portion 16A of the sanitiser 10 and specifically the base of the sanitiser 10, it will be appreciated the outlet 36 can be located in any location suitable for providing plasma 22 to the user for sanitising the user. The sanitiser 10 may supply plasma to the user for sanitising a user's hands.

The embodiment of FIG. 1 may include an optional drier 60 that may include a fan 66 and a motor 68 for supplying air to an outlet 64 for directing air to a user. The drier 50 shown in FIG. 1 is a jet drier 60 that provides ambient temperature air at high velocity for drying the user. However, it will be understood that any other form of drier 60 including a hot air drier 60 further including a heater 62 may be used. The outlet of the drier 64 may be positioned proximal, next to or adjacent the second outlet 36 of the sanitiser 10 such that the user does not need to move, or must move only a very short distance, to receive the air from the drier 60 or the plasma 22 from the sanitiser 10. The second outlet 36 may surround the outlet of the drier 64 or visa-versa for directing plasma towards a user. Surrounding the outlet may be a coaxial arrangement, or a plurality of outlets 36, 64 surrounding a central outlet 36, 64. For Example the second outlet 36 may include two outlets either side of the drier outlet 64. The outlets 36, 64 may be configured to direct fluid in a convergent path in order to reduce the perceived difference between drying air and plasma 22 delivery or to better surround the user's hands with fluid for sanitising or drying. The drier 60 may be a hand drier 60.

Figure 2:
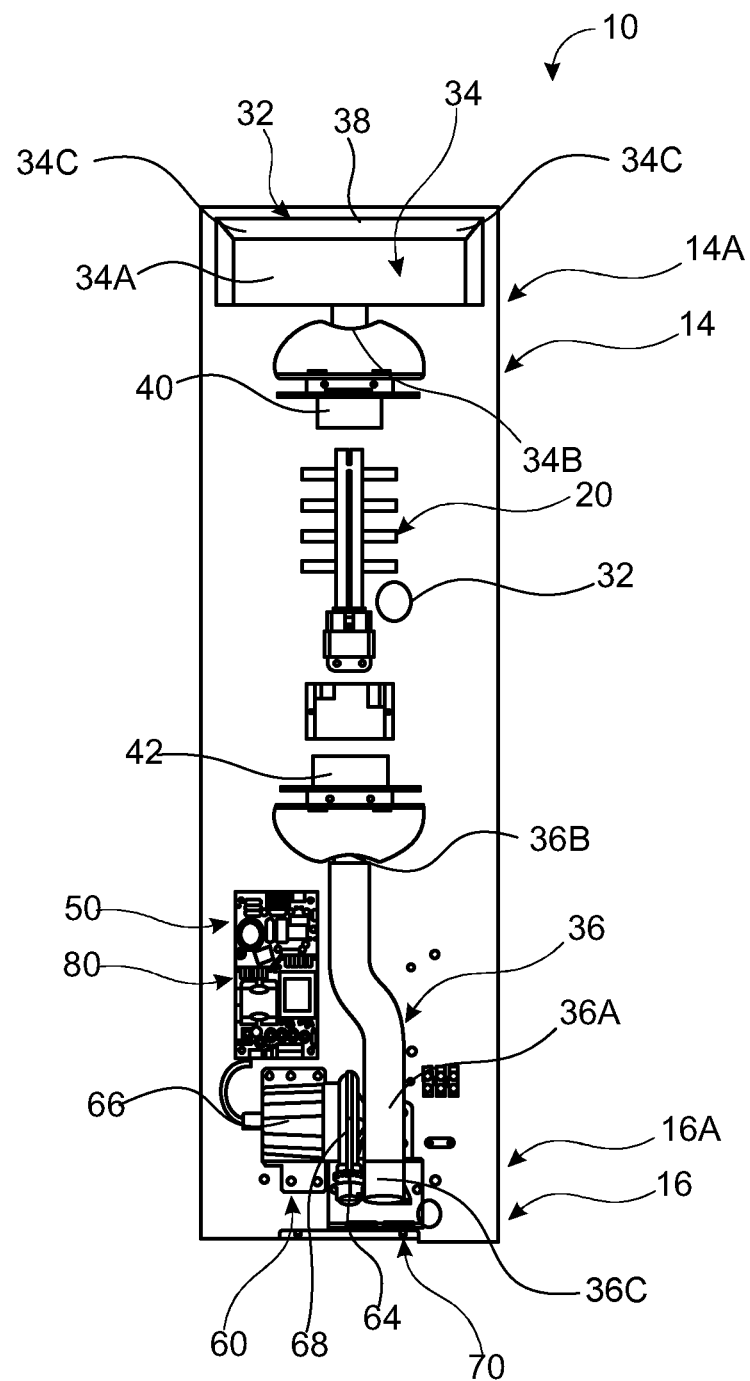
FIG. 2 shows the steriliser including a high-speed jet drier with the external casing and the reservoir removed.

FIG. 2 shows a similar embodiment of the sanitiser 10 of FIG. 1 with the external cover 12 removed and the reservoir 30 removed. Removing the reservoir 30 exposes the plasma generator 20, the one or more inlets 32 and one or more fluid movers 40, 42. In the embodiment of FIG. 2 the plasma generator 20 may be contained within the reservoir 30, however may be remote from the reservoir 30.

The plasma generator 20 may include an Ultraviolet light (UV) source 24 and photo-catalytic plates 26. The UV has a dual effect. UV light, specifically short wavelength ultraviolet light known as UV-C kills or deactivates pathogens directly exposed to the UV light by destroying or disrupting their genetic material, therefore, sanitising the fluid that passes through the reservoir that is directly exposed to the UV light. The plasma generator 20 also generates plasma 22. The photo-catalytic plates 26 may include the material Titanium Dioxide, that when exposed to UV light cause water molecules in the air to oxidise to form Hydroxyl radicals and super oxide ions in the air. The Hydroxyl radicals have anti-bacterial and anti-viral effects by damaging the molecular structure of the pathogens. The super oxide ions cause small particles such as viruses to clump together and form clusters. Thus, removing them from the atmosphere. The advantage of the hydroxyl radicals and the super oxide ions are that they are effective outside of the sanitiser 10 in which they are created and permeate the ambient surroundings or room in which the sanitiser 10 is located and therefore sanitise the air and surfaces and the item or user that are external to the sanitiser 10. The purpose of the reservoir 30 is to create a mixture of air and plasma 22 with a high concentration of plasma 22, comprised of hydroxyl radicals and super oxide ions, to provide an improved sanitising effect for the user or item outside of the sanitiser 10.

The sanitiser 10 may include one or more fluid movers 40, 42 for moving and directing fluid through the sanitiser 10. FIG. 2 shows an embodiment with 2 fluid movers 40, 42. The first outlet 34 may include the first fluid mover 40 for supplying plasma 22 to the first outlet 34. The second outlet 36 may include the second air mover 42 for supplying plasma 22 to the second outlet 36.

The embodiment of FIG. 2 may also include a separate one or more inlets 32 connected to the plasma generator 20. Note a separate inlet 32 is not included in the embodiment of FIG. 1. In the embodiment of FIG. 1 when the first fluid mover 40 is supplying plasma 22 from the reservoir 30 to the outlet 34 air enters the outlet 36 and outlet 36 performs the function of the one or more inlets 32 and when the second fluid mover 42 is supplying plasma 22 to the outlet 36 air enters outlet 34 and outlet 34 preforms the function of the one or more inlets 32.

Whilst it will be appreciated that the plasma generator 20 in the preferred embodiment of FIG. 2 is contained within the reservoir 30 the plasma generator 20 may be contained within the inlet 32 or another position for generating plasma 22 to be stored in the reservoir 30 and outputs 34 and 36.

In the embodiments shown there are two fluid movers 40, 42. However, in an alternative embodiment one or more fluid movers 40, 42 may be included. A first fluid mover 40 may be located at the first outlet 34 of the reservoir 30 for causing flow of plasma 22 out of the first outlet 34. A second fluid mover 42 may be located at the second outlet 36 of the reservoir 30 for causing the flow of plasma 22 out of the second outlet 36. An alternative embodiment is envisaged wherein there is only one fluid mover 40, 42 for example only the first fluid mover 40 or the second fluid mover 42 for supplying plasma 22 to both the first outlet 34 and the second outlet 36. In such an embodiment the fluid mover 40, 42 may be a bi-directional fluid mover 40C. The one or more fluid movers 40, 42 may include one or more fans 40A, 42A and one or more motors 40B, 42B for causing flow of air and/or plasma into or from outlets 34, 36 or one or more inlets 32. The fluid movers 40, 42 may each include a director 40D, 42D for obturating or partially obturating the outlets 34, 36 or the inlet 32 to prevent or impede flow of plasma from said outlets 34, 36 or the inlet 32.

In a preferred embodiment the first fluid mover 40 for supplying plasma 22 to the first outlet 34 supplies a low volume flow that may be suitably matched to the speed of plasma generation by the plasma generator 20 and the second fluid mover 42 may supply a higher volume of stored plasma 22 from the reservoir 30 to the second outlet 36. Therefore, the first fluid mover 40 may be smaller than the second fluid mover 42.

A controller 50 comprising a timer 80, a presence sensor 70 and a gas sensor 72 are also visible in FIG. 1 and FIG. 2. The timer 80 may also be separate from the controller 50. The timer 80, the sensor 70, the one or more air movers 40, 42 and the drier 60 if present are all communicatively and/or operatively connected to the controller 50. The controller 50 may be operably connected to the one or more fluid movers 40, 42 for causing the flow of plasma 22 from the reservoir 30 to one or both of the outlets 34 and 36. The controller 50 may be operably connected to the one or more air movers 40, 42 to prevent or not actively cause the flow of plasma 22 from the reservoir 30 and/or the outlets 34, 36. The controller 50 may be operably connected to the one or more air movers 40, 42 to prevent the flow of plasma 22 from the reservoir 30 by preventing operation of the one or more air movers 40, 42 or by causing the air movers 40, 42 to obturate or partially obturate both or either of the outlets 34 and 36. The controller 50, in response to a signal received from the presence sensor 70 indicating the present of the user may activate the timer 80 and cause any one or any combination of the above actions of the one or more air movers 40, 42 in response to one or more of a signal from the presence sensor 70 and information from the timer 80. The gas sensor 72 may be a gas concentration sensor 72. The gas sensor 72 may detect a particular gas or particular gases and send a signal to the controller 50 indicating the presence or concentration of that gas or gases to the controller 50. The controller 50 may include a gas concentration threshold for each particular gas and a comparator 52 for comparing the concentration of the particular gases with the threshold gas concentration and indicating to the controller 50 if the concentration of the particular gas exceeds the gas concentration threshold. The comparator 52 may also indicate to the controller 50 if the concentration is at or passes the threshold and in response the controller may control the plasma generator 20. Controlling the plasma generator 20 can include activating or deactivating the plasma generator 20. Whilst it is stated above that the controller 50 includes the concentration threshold and the comparator 52, their relative location is immaterial. For example, the comparator 52 and the threshold may be included in the gas sensor 72. In response to the presence of the particular gas the controller 50 may deactivate the plasma generator 20; alternatively, if the comparator 52 sends a signal to the controller 50 indicating that the concentration of the particular gas has reached or exceeded the gas concentration threshold the controller 50 may deactivate the plasma generator. Once the particular gas is no longer detected, or the concentration of the gas falls below the threshold, the sensor 72 or the comparator 52 may signal the fact to the controller 50 and the controller 50 may activate the plasma generator 20. In short, the sanitiser 10 may include closed loop control of the concentration of the particular gas. The gas sensor 72 may be located on the exterior of the sanitiser 10 for monitoring the ambient air surrounding the sanitiser 10 or it may be located on the inlet 37 of the sanitiser 10.

The particular gas may be Ozone which can be produced as a result of the super oxide ions released by the sanitizer. Therefore, turning the plasma generator 20 on and off can regulate the concentration of Ozone gas.

Figure 3:
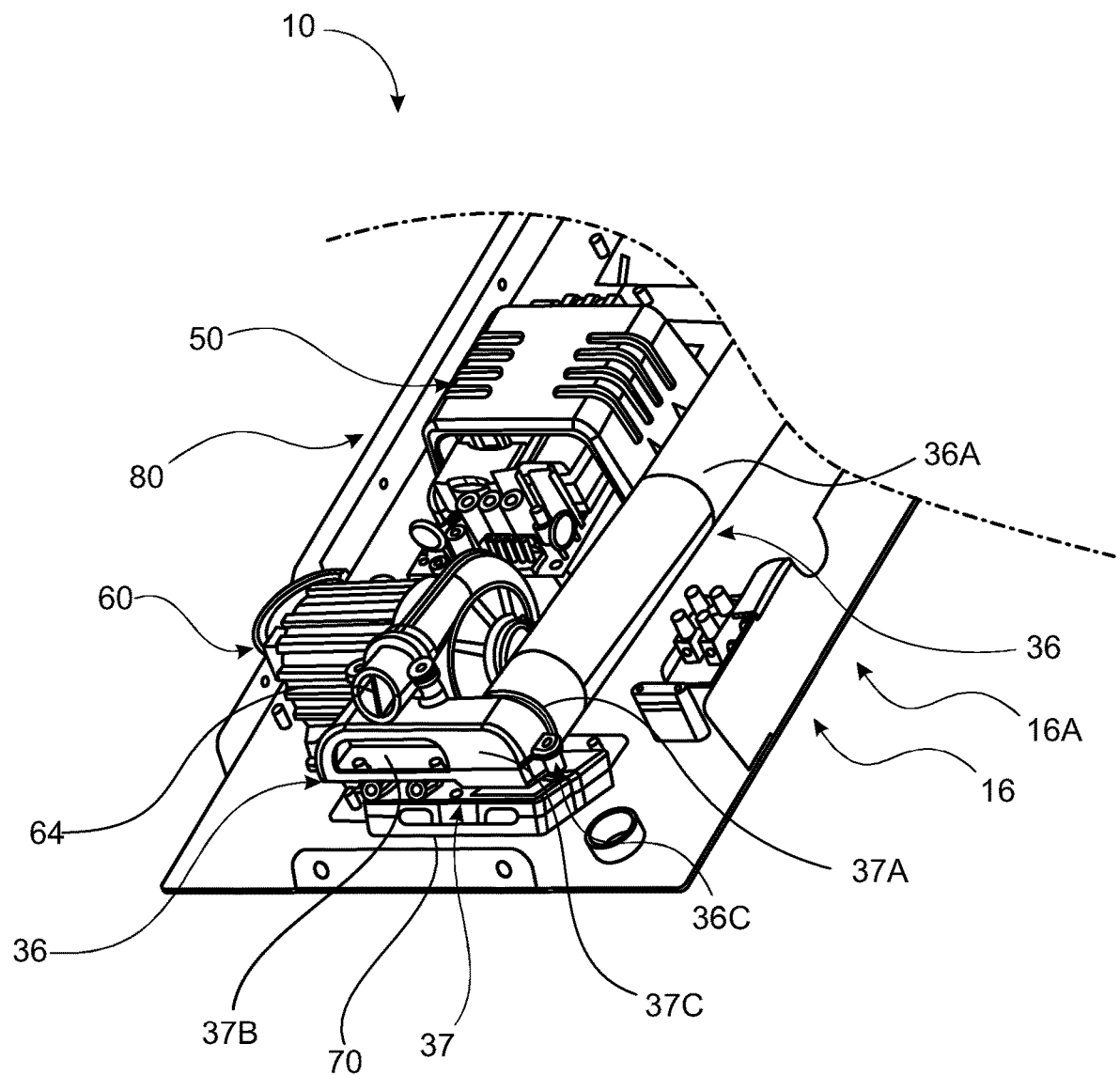
FIG. 3 shows a partial view of a steriliser similar to FIG. 1 displayed at an angle to view the lower portion from below therefore showing the outlet plenum.

FIG. 3 shows an alternative embodiment of the sanitizer 10 tilted back to display the second portion 16 that in this embodiment is the lower portion 16A. The embodiment of FIG. 3 is similar to the embodiment of FIG. 1 with the addition that the second outlet 36 includes an outlet plenum 37. The outlet plenum is a chamber for controlling the velocity of the plasma 22, supplied by the one or more fluid movers 40, 42 and directing it to the user. The outlet plenum 37 has an inlet 37A, a body 37B and an outlet 37C. The outlet 37C may be offset from the inlet 37A. The outlet 37C may be laterally offset from the inlet 37A and/or of greater area than the inlet 37A to reduce the output velocity of the plasma 22, deliver plasma 22 over a greater area and/or introduce turbulent flow in order to improve the distribution over the user to enhance the sanitising effect. In such an arrangement the drier outlet 64 may be positioned in front of the second outlet 36 or visa-versa.

Figure 4:
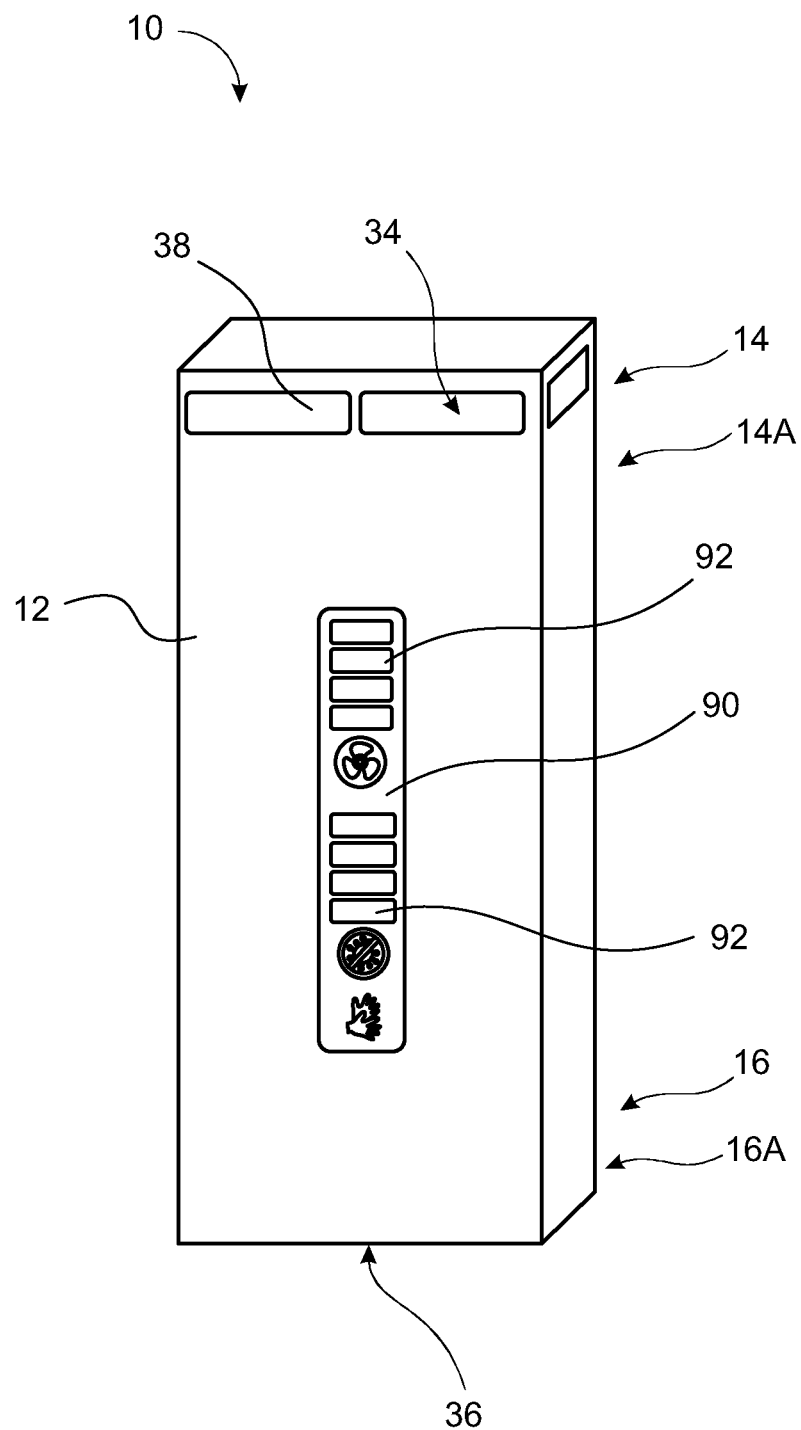
FIG. 4 shows the steriliser with the outer casing in place.

FIG. 4 shows the sanitiser 10 fully assembled in a preferred embodiment including an external casing 12 comprising an upper portion 14A, a lower portion 16A, and a display 90 for indicating to the user the proportion of time remaining until the sanitising process is complete, the time remaining and/or that sanitising is complete. The display 90 may be operably connected to one or more of the controller 50 and/or the timer 80. The display 90 may include a plurality of LEDs 92, wherein the proportion of time remaining until sanitising is complete is indicated by illuminated LEDs 92. Said LEDs 92 extinguishing in sequence as the time remaining diminishes. Alternatively, the display 90 may include a numerical count down. When a drier 60 is fitted the display 90 may include the time the drier 60 is active when displaying the time remaining.

FIG. 4 also shows the divergent outlet 38 of the first outlet 34 emerging in the upper portion 14A of the external case 12 however it will be understood that in alternative embodiments the first outlet may emerge towards the lower portion 16A or any other location suitable for providing plasma to the ambient surroundings for sanitising said ambient surroundings. In this case the divergent outlet 38 has 4 apertures 38A but any number of apertures 38A is possible. In the embodiment of FIG. 4 the second outlet 36 emerges from the lower portion 16A of the external case 12 for supplying plasma 22 to a user, in particular from the base of the sanitiser 10. In other embodiments the second outlet 38 may emerge from any position suitable for sanitising the user.

Figure 5:
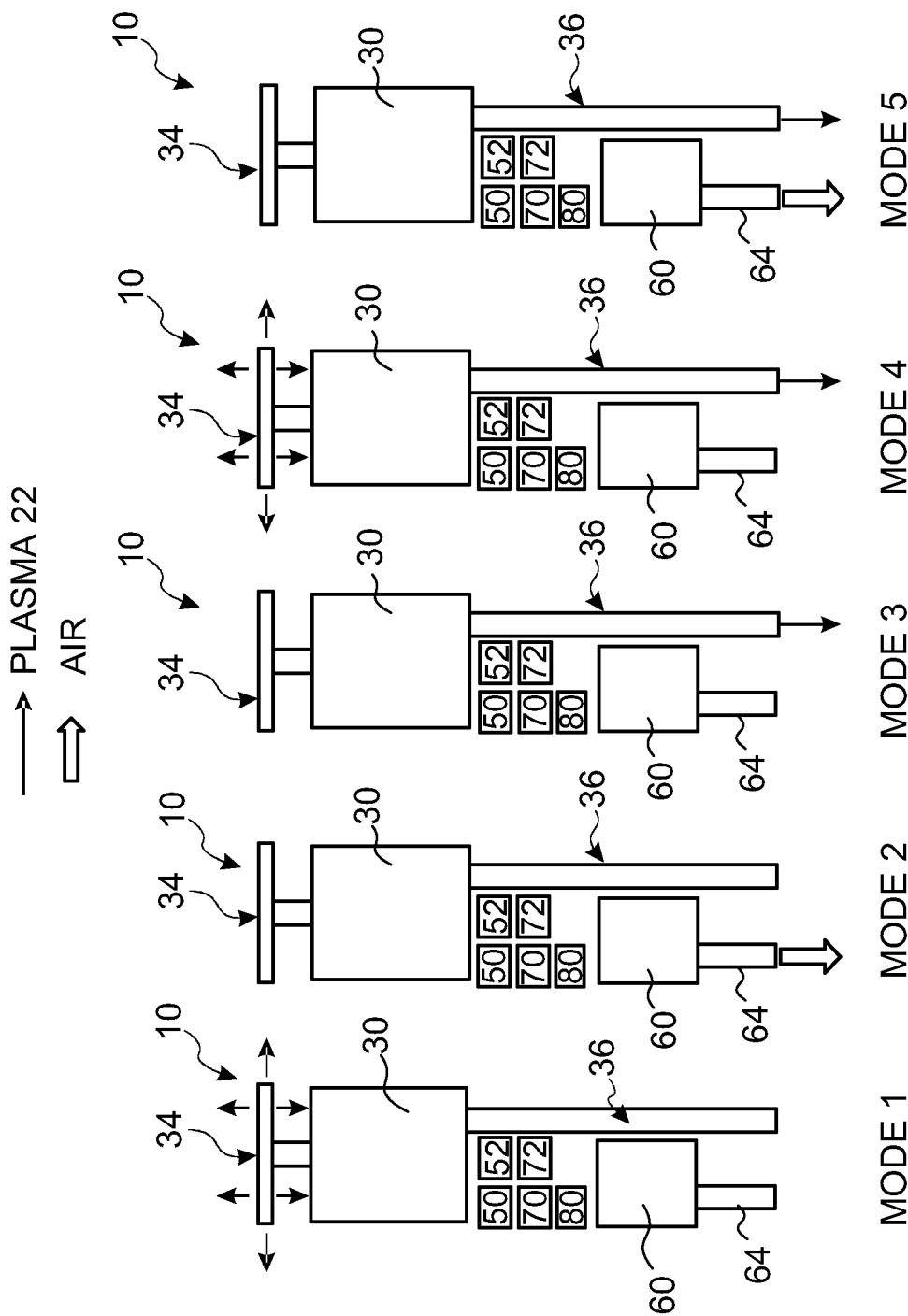
FIG. 5 shows a schematic of the fluid flow in the various modes of operation of the steriliser.

FIG. 5 shows modes of operation of the sanitiser 10.

In a first mode the controller 50 may operate the one or more fluid movers 40, 42 to cause the flow of plasma out of the first outlet 34 alone for sanitising the ambient surroundings of the sanitiser 10. In a preferred embodiment the controller 50 activates the first fluid mover 40 to cause the flow of plasma out of the first outlet 34 alone. In the first mode air flows into the intake 32 and plasma 22 generated by the plasma generator 20 flows out of the first outlet 34. In a preferred embodiment the air flows into the intake 32 comprising the second outlet 36.

In a second mode the controller 50 may prevent operation of the one or more fluid movers 40, 42 thereby ceasing movement of fluid through the reservoir 30 and storing the plasma 22 generated by the plasma generator 20 in the reservoir 30. Alternatively, the controller 50 may cause the fluid movers 40, 42 to obturate the outlets 34, 36. If present, in the second mode, the drier 60 may be activated by the controller 50 for drying the user. When in the second mode the reservoir 30 of the sanitiser 10 stores the plasma 20 generated by the plasma generator 20. In the second mode plasma 22 is built up within the reservoir 30, to provide a high concentration of plasma 22 in the air and plasma mixture to provide an improved sanitising effect when the plasma 22 is directed at a user or item to be sanitised in the air outside of the sanitiser 10.

In a third mode the controller 50 activates the one or more fluid movers 40, 42 to cause the flow of plasma 22 out of the second outlet 36 alone, for sanitising the user after deactivating the dryer 60 if its operation is detected. In a preferred embodiment the controller 50 activates the second fluid mover 42 to cause the flow of plasma out of the second outlet 36. In the third mode air flows in the inlet 32 and plasma flows out of the second outlet 36. In an embodiment the air flows in the inlet 32 comprising the first outlet 34.

In a fourth mode the controller 50 may activate the one or more fluid movers 40, 42 to cause the flow of plasma 22 out of the first outlet 34 and the second outlet 36 simultaneously. In the fourth mode air flows in the intake 32 and plasma flows out of the first and second outlets 34, 36.

In a fifth mode the controller 50 may activate the one or more fluid movers 40, 42 to cause the flow of plasma out of the second outlet 36 for sanitising the user and activate the drier 60 concurrently.

The modes of operation can occur in any order under the control of the controller 50. In a preferred embodiment the controller 50, on receiving a signal from the presence sensor 70, indicating the presence of a user has been detected, may cause the first mode, the second mode and the third mode or the second mode and third mode to occur in sequence or only the second mode for a period of time. The first mode may be a default or standby mode for sanitising the room or ambient surroundings of the sanitiser 10 to which the controller 50 returns the sanitiser 10 after being in other modes when no user is detected by the presence sensor 70. On receipt of a signal from the presence sensor 70 indicating presence of a user the controller 50 may cause the sanitiser 10 to move to the second mode to store plasma in preparation for sanitising the user and may further activate the timer 80. The controller 50 may cause the sanitizer 10 to move to the third mode once sufficient time has elapsed and/or sufficient plasma is stored in the reservoir 30 to sanitise the user. The controller 50 in communication with the timer 80 may, after a predefined period, cause the sanitiser to move from the second mode to the third mode to sanitise the user using the plasma from the reservoir 30 accumulated during the second mode.

In an embodiment including a drier 60 the controller will activate the drier during the second mode so that the user may be dried or dry themselves whist waiting for the reservoir to accumulate sufficient plasma for the sanitiser 10 to sanitise the user in the third mode.

Figure 6:
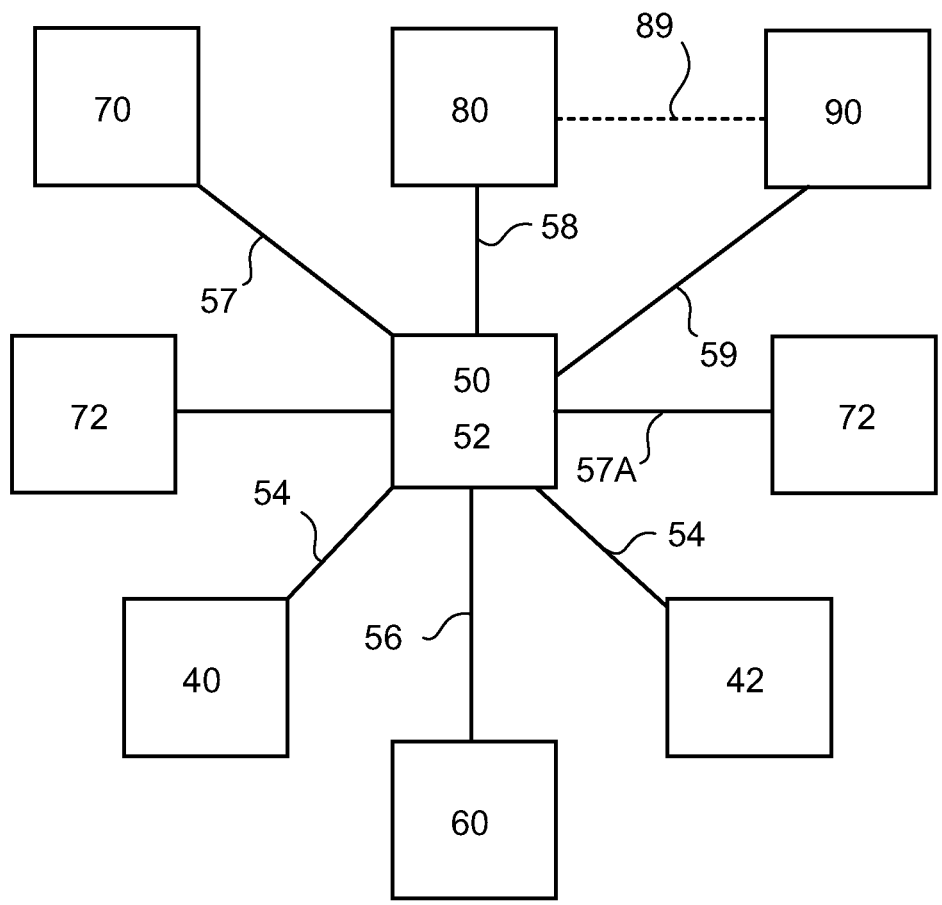
FIG. 6 shows a schematic of the connections of the controller within the sanitiser.

FIG. 6 shows a schematic of the connections between the controller 50 which may include the comparator 52 and the presence sensor 70, the gas sensor 72 if fitted, the timer 80, the display 90, the air movers 40, 42 and the drier 60.

There may be a connection 54 between the controller 50 and the one or more fluid movers 40, 42, that may be an electrical connection 54 for powering the one or more fluid movers 40, 42 or it may be a signal connection 54 for passing signals from the controller 50 to the one or more fluid movers 40, 42 for activating and deactivating the fluid movers 40, 42. The signal connection 54 may also control the speed of the fluid movers 40, 42 or cause the fluid movers 40, 42 to obturate the one or more outlets 34, 36 or one or more inlets 32. The signal connection 54 may also pass information on the status of the one or more fluid movers 40, 42 to the controller 54.

There may be a connection 56 between the controller 50 and the drier 60 that may be an electrical connection for powering the drier 60 or may be a signal connection 56 for controlling the drier or receiving signals at the controller 50 from the drier 60 regarding the status of the drier 60.

There may be a connection 57 between the controller 50 and the presence sensor 70. The connection 57 may be a signal connection 57 for providing the controller 50 with a signal indicating the presence of a user.

There may be a connection 57a between the controller 50 including the comparator 52 and the gas sensor 72. The connection 57a may be a signal connection 57 for providing the controller 50 with a signal indicating the presence or concentration of a particular gas.

There may be a connection 58 between the timer 80 and the controller 50 that is a signal connection 58 for providing signals from the controller 50 to the timer 80. For example, to start the timer if the controller 50 receives a signal presence sensor 70 indicating the presence of a user. The signal connection 58 may also provide timing signals from the timer 80 to the controller 50.

There may be a connection 59 between the controller 50 and the display 90. The connection 59 may be a signal connection 59 for providing timing or status information to the display 90. Alternatively, or in addition there may be a connection 89 direction between the timer and the display 90 that may also be a signal connection 89 for passing timing information from the timer 80 to the display 90.

In Operation

By default, the sanitiser 10 may be in the first mode described above to sanitise the ambient surroundings of the sanitiser 10. On sensing the presence of a user, the presence sensor 70 senses a signal to the controller 50. The presence sensor 70 may sense the user entering the room or the presence of the user at the sanitiser 10 or the presence of the user, in particular the hands of a user, in front of the second outlet 36. On receipt of the signal from the presence sensor 70 indicating the presence of the user the controller 50 may activate the timer 80 and cause the sanitiser 10 to operate in the second mode in order to store plasma 22 in preparation for sanitising the user. Thus, at the end of the period in the second mode a high concentration of plasma 22 is available to sanitize the user. If included the drier 60 may be activated during the second mode for drying the user.

The drier may be for drying the user's hands. After a period of time has elapsed, this may be a pre-defined period of time, that may be sufficient for the aforementioned actions of the second mode to be completed the controller 50 may on receipt of a signal from the timer 80 or from an input from the user move to the third mode. In the third mode the plasma 22 stored in the reservoir 30 during the period in the second mode is directed to the user via outlet 36 in order to sanitise the user. Once sanitising is complete the display 90 in response to a signal from the controller 50 and/or the timer 80 will indicate to the user that the sanitising process is complete and the controller 50 will return the sanitiser to the first mode.

The controller 50 may include a processor and a memory and the functions of the controller 50 and/or the timer 80 can by implemented using software and/or hardware.

Any system feature, as described herein may also be provided as a method feature, and vice versa. As used herein, means plus function features may be expressed alternatively in terms of their corresponding structure.

Any feature in one aspect or embodiment may be applied to other aspects, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects can be implemented and/or supplied and/or used independently.

The invention claimed is:

1. A sanitiser having an external casing, a first portion and a second portion, further comprising:

a plasma generator, for generating a plasma;
a reservoir, for storing gaseous plasma generated by the plasma generator prior to use and having one or more inlets connected to the plasma generator and the reservoir further including a first and a second outlet connected to an environment outside the sanitiser for discharging plasma from the reservoir,
one or more fluid movers, for causing movement of the gaseous plasma,
a controller, for controlling the one or more fluid movers such as to cause storing of plasma and the flow of gaseous plasma from the reservoir out of one or other or both of said outlets;
wherein the sanitiser includes a timer connected to the controller and the controller is operable to cause the fluid movers to cease moving fluid and the reservoir to store plasma for at least a pre-defined time period of the timer; and
wherein after the time period of the timer has elapsed, the controller is operable to cause the fluid movers to move an increased concentration of plasma from the reservoir out of the first outlet, the second outlet, or both the first and second outlets.

2. The sanitiser as claimed in claim 1, wherein said plasma generator is contained within the reservoir.

3. The sanitiser as claimed in claim 1, wherein said sanitiser has an upper portion and a lower portion and wherein said first outlet of the reservoir comprises a divergent outlet towards the upper portion of the sanitiser for directing gaseous plasma generally outwardly and downwardly from the sanitiser.

4. The sanitiser as claimed in claim 1 and further including a dryer.

5. The sanitiser as claimed in claim 1 and further including a dryer comprising a jet dryer for creating a jet of air and an outlet for directing said air towards a user and wherein said second outlet of the reservoir is positioned proximal to the dryer outlet for directing gaseous plasma towards a user.

6. The sanitiser as claimed in claim 1 and further including a dryer comprising a heater for heating air and an outlet for directing said heated air towards a user and wherein said second outlet of the reservoir is positioned proximal to the dryer outlet for directing gaseous plasma towards the user.

7. The sanitiser as claimed in claim 1 and further including a dryer and a dryer outlet for directing said air towards a user wherein said second outlet from the reservoir surrounds the dryer outlet.

8. The sanitiser as claimed in claim 1, wherein said second outlet includes an outlet plenum comprising a plenum inlet and a plenum outlet, the plenum outlet offset from the plenum inlet to slow the velocity and control the direction of gaseous plasma directed to the user.

9. The sanitizer as claimed in claim 1, wherein said controller is operable in a first mode to cause the operation of the one or more fluid movers such as to cause the flow of plasma out of said first outlet alone.

10. The sanitiser as claimed in claim 1, wherein said controller is operable in a third mode to cause the operation of the one or more fluid movers such as to cause the flow of plasma out of the second outlet alone.

11. The sanitiser as claimed in claim 1, wherein said controller is operable in a fourth mode to cause the operation of the one or more fluid movers such as to cause the flow of plasma out of both the first and second outlets simultaneously.

12. The sanitiser as claimed in claim 1, including a presence sensor for sensing the presence of a user and wherein said controller is operably connected to said sensor for receiving a signal upon the detection of a user.

13. The sanitiser as claimed in claim 12, wherein said controller is operably connected to the presence sensor and to the one or more fluid movers for ceasing operation thereof and, thereby, preventing flow of gaseous plasma from said reservoir for a period of time upon the detection of a user.

14. The sanitiser as claimed in claim 4, including a presence sensor for sensing the presence of a user and wherein said controller is operably connected to said sensor for receiving a signal upon the detection of a user; wherein said controller is operably connected to the dryer for detecting operation thereof and is operably connected to the presence sensor and to the one or more fluid movers for allowing the flow of plasma from said reservoir out of said second outlet and towards the user upon cessation of the flow of air from the dryer.

15. The sanitiser as claimed in claim 1, wherein said controller is operable upon receipt of a signal from the presence sensor to operate the one or more fluid movers to cause gaseous plasma to be directed out of said first outlet when no user is detected.

16. The sanitiser as claimed in claim 12, wherein said controller is operable upon receipt of a signal from the presence sensor to operate the one or more fluid movers to cause gaseous plasma to be directed out of said first outlet when a user is detected.

17. The sanitiser as claimed in claim 1, wherein said one or more fluid movers comprise one or more fans.

18. The sanitiser as claimed in claim 17, wherein a first fan of said one or more fans is at the first outlet to the reservoir whilst a second fan of said one or more fans is at the second of said outlets to the reservoir.

19. The sanitiser as claimed in claim 1, wherein said one or more fluid movers from the reservoir comprise a single bi-directional fan.

20. The sanitiser as claimed in claim 1, wherein said one or more inlets to the reservoir comprises one or other of the first and second outlets.

21. The sanitiser as claimed in claim 4, wherein the controller along with the timer cause operation of the one or more fluid movers at a set time after cessation of flow from the hand dryer.

22. The sanitiser as claimed in claim 1 further including a display for informing the user when a sanitising process is complete, wherein the display comprises a plurality of LEDs for indicating the time remaining until the sanitising process is complete.

23. The sanitiser as claimed in claim 1 further including a gas sensor for detecting the concentration of a particular gas, operably connected to the controller, the controller including a comparator for comparing a gas concentration threshold for the particular gas with the concentration of the particular gas detected by the gas sensor and operable to activate or deactivate the plasma generator when the concentration of the particular gas is at or passes the gas concentration threshold.

24. The sanitiser according to claim 23, wherein the controller is operable to deactivate the plasma generator if the concentration of the particular gas is at or above the gas concentration threshold.

25. The sanitiser according to claim 23, wherein the particular gas is ozone.

26. The sanitiser as claimed in claim 1 for sanitising hands of a user.

27. The sanitiser as claimed in claim 4, wherein the dryer is a hand dryer.

\* \* \* \* \*